(12) United States Patent
Miller et al.

(10) Patent No.: US 9,086,342 B2
(45) Date of Patent: Jul. 21, 2015

(54) EMISSIONS MEASURING SYSTEM

(75) Inventors: David W. Miller, Clarence, NY (US);
Brian J. Beckmann, Buffalo, NY (US);
Aaron G. Alexander, Eden, NY (US);
William Earl Leatherland, Jr., Buffalo, NY (US)

(73) Assignee: Global MRV, Inc., Riverhead, NY (US)

( * ) Notice: Subject to any disclaimer, the term of this patent is extended or adjusted under 35 U.S.C. 154(b) by 533 days.

(21) Appl. No.: 13/420,058

(22) Filed: Mar. 14, 2012

(65) Prior Publication Data

US 2012/0239308 A1 Sep. 20, 2012

Related U.S. Application Data

(60) Provisional application No. 61/453,424, filed on Mar. 16, 2011.

(51) Int. Cl.
*G01N 21/3504* (2014.01)
*G01N 1/22* (2006.01)
*G01N 33/00* (2006.01)

(52) U.S. Cl.
CPC .......... *G01N 1/2252* (2013.01); *G01N 21/3504* (2013.01); *G01N 33/0075* (2013.01)

(58) Field of Classification Search
CPC ................................................. G01N 21/3504
USPC .......................................................... 702/24
See application file for complete search history.

(56) References Cited

U.S. PATENT DOCUMENTS

| | | | |
|---|---|---|---|
| 4,922,714 A | | 5/1990 | Grob |
| 5,099,680 A | * | 3/1992 | Fournier et al. ............... 73/23.31 |
| 5,105,651 A | * | 4/1992 | Gutmann ...................... 73/23.31 |
| 5,993,743 A | | 11/1999 | Nordman |
| 6,308,130 B1 | | 10/2001 | Vojtisek-Lom |
| 6,387,706 B1 | | 5/2002 | Eden |
| 6,435,019 B1 | | 8/2002 | Vojtisek-Lom |
| 6,629,453 B1 | | 10/2003 | Surnilla |
| 2002/0157482 A1 | * | 10/2002 | Silvis et al. ..................... 73/864 |
| 2004/0168504 A1 | * | 9/2004 | Eden et al. ..................... 73/23.2 |
| 2006/0009889 A1 | | 1/2006 | Bernard |
| 2006/0180371 A1 | | 8/2006 | Breed |

(Continued)

FOREIGN PATENT DOCUMENTS

| | | |
|---|---|---|
| DE | 102007042749 A1 | 3/2009 |
| JP | 2002071527 | 3/2002 |
| KR | 10-0804019 B1 | 2/2008 |

OTHER PUBLICATIONS

International Search Report and Written Opinion of the International Searching Authority, Korean Intellectual Property Office, dated Jun. 29, 2012.

*Primary Examiner* — Bryan Bui
(74) *Attorney, Agent, or Firm* — Phillips Lytle LLP

(57) ABSTRACT

An improved apparatus for sensing exhaust emissions (15) comprising a passive induction sampler (50) configured to sample exhaust from a source (16), a processing unit (30) connected to the induction sampler and configured to be mounted in close proximity to exhaust from the source, the processing unit comprising an input port (31) adapted to receive flow from the passive induction sampler, an output port (32), a flow path (33) between the input port and the output port, a sensor (34) for sensing one or more pollutants in the flow path, a processor (37) configured to receive measurements from the sensor, a power source (39), and a wireless transmitter (36) connected to the processor.

30 Claims, 11 Drawing Sheets

(56) References Cited

U.S. PATENT DOCUMENTS

| | | |
|---|---|---|
| 2008/0154671 A1 | 6/2008 | Delk |
| 2010/0199637 A1 | 8/2010 | Powell |
| 2010/0292934 A1* | 11/2010 | Stark et al. ............... 702/24 |
| 2012/0180548 A1* | 7/2012 | Bosselmann ............ 73/23.31 |

* cited by examiner

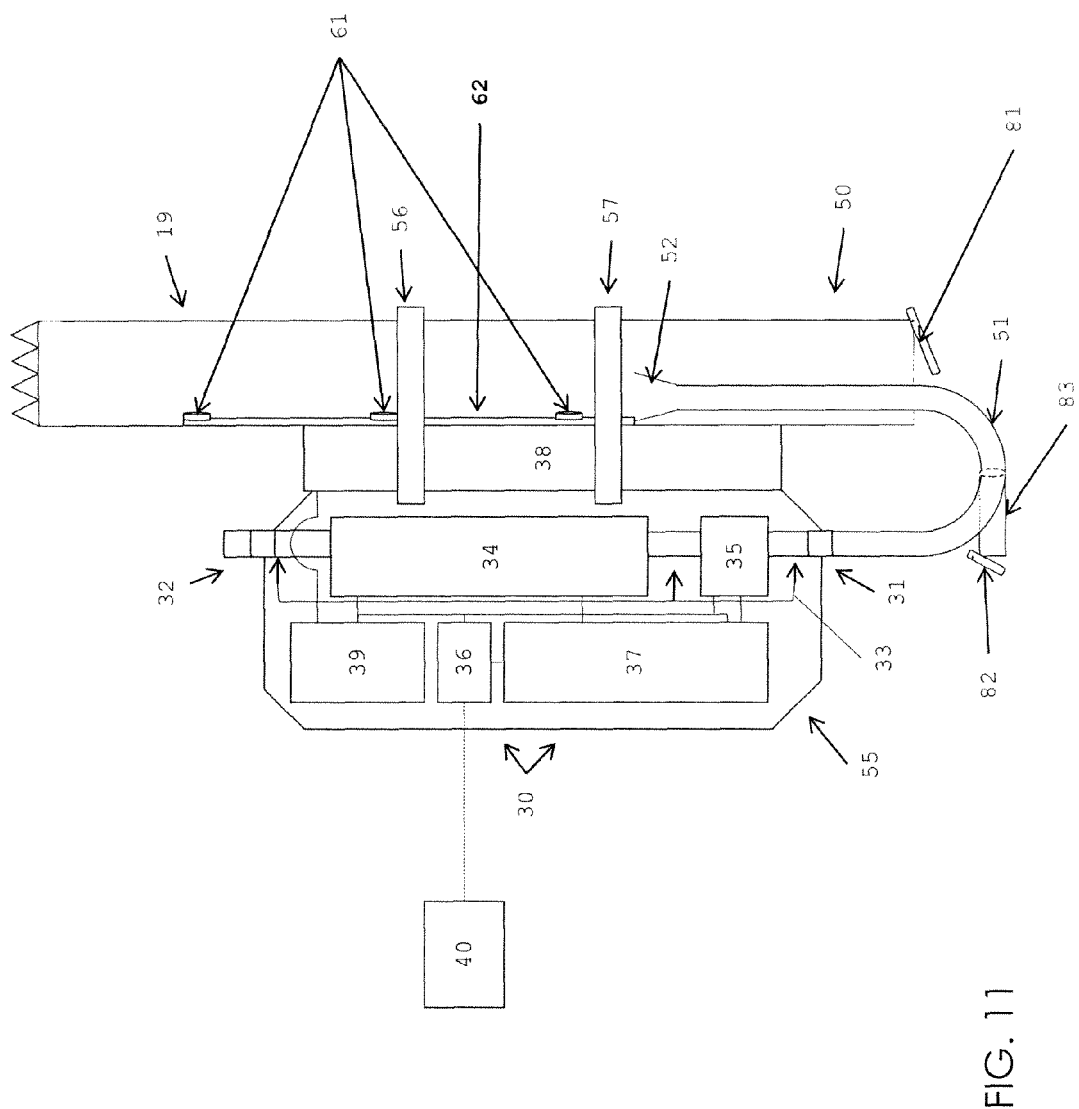

EMISSIONS MEASURING SYSTEM

TECHNICAL FIELD

The present invention relates generally to the field of vehicle emissions measuring systems and, more particularly, to an improved on-board emissions measuring system.

BACKGROUND ART

Motor vehicle emissions are a leading source of air pollution in many metropolitan areas. As a result, considerable effort and resources are currently devoted to various emission reduction strategies, such as emission inspection programs, reformulated or alternative fuels, stricter standards for new vehicles, mass transit, improved engine control and catalyst technologies, upgrade and repair of existing vehicles, and emission reduction credits aimed at providing a financial incentive to reduce emissions. However, in order to evaluate the impact of these reduction strategies and take advantage of emissions credits, it is necessary to measure and collect accurate real-world emission measurements over the life of a vehicle.

It is known that emission testing may be performed in a specialized laboratory, where the vehicle is driven on a dynamometer according to a prescribed driving cycle, such as I/M 240 or FTP for light and medium duty vehicles and CBD for heavy duty vehicles. This approach has several significant disadvantages, including that the driving cycles do not adequately represent real-world driving conditions, which vary and are often unknown.

Mobile testing systems that are attached to the vehicle are also known. For example, an on-board testing system mounted on a dedicated instrumented vehicle was disclosed by Sierra Research. This system used a repair-grade four-gas non-dispersive infra-red (NDIR) analyzer to measure exhaust gas concentrations and several sensors mounted on the engine to determine intake air flow. From these measurements, exhaust mass flow and mass emissions can be computed.

A simpler system, using repair grade NDIR analyzer concentration data only, was developed at the University of Denver to predict I/M 240 mass emissions. Using this system, the average ratio of pollutant to fuel consumed can be calculated from the concentration data. The amount of fuel consumed can then be estimated from the length of the trip and fuel economy. While this method was successful in predicting whether a vehicle would pass or fail an I/M 240 test, and has been incorporated into newer repair grade analyzers, it was not sufficiently accurate in measuring actual mass emissions, since it did not properly account for emissions during extreme (high or low) exhaust flow.

In recent years a number of portable emissions measurement systems (PEMS) have been developed. A PEMS is an onboard testing system or device that measures the emissions from mobile source while the source is an actual, real-world use, rather that in a laboratory or simulated environment.

The AXION™ device manufactured by GlobalMRV, Inc., of 3000 Sound Avenue, Riverhead, N.Y. 11901, is a commercially available PEMS. This system is capable of measuring mass emissions on a variety of vehicle engines during actual, real world and regular use and operation. The unit provides HC, CO, $CO_2$, $NO_x$ and $O_2$ readings for gasoline powered vehicles and $NO_x$, CO, $CO_2$, $O_2$ and PM (light scattering) readings for diesel vehicles. The pollutant concentrations are obtained from a sample probe inserted into the tail pipe. This data is then combined with exhaust flow data calculated using engine parameters read from the vehicles engine control unit to determine mass emissions.

U.S. Pat. No. 6,308,130, entitled "Portable On-Board Mass Emissions Measuring System," discloses a PEMS for measuring mass emissions. U.S. Pat. No. 6,435,019, entitled "Portable On-Board System for Measuring Vehicle Exhaust Particulate Emissions," discloses a PEMS that measures emissions of particulate matter. The disclosure of each of U.S. Pat. No. 6,308,130 and U.S. Pat. No. 6,435,019 are incorporated in their entirety herein by reference.

The SPOT unit provided by Analytical Engineering, Inc., of 2555 Technology Boulevard, Columbus, Ind. 47201, is another commercially available PEMS. The SEMTECH® unit provided by Sensors, Inc., of 6812 S. State Road, Saline, Mich. 48176, is yet another alternative. For particulate matter, the SCANNING MOBILITY PARTICLE SIZER™ manufactured by TSI, Inc., of 500 Cardigan Road, Shoreview, Minn. 55126, is another commercially available PEMS system. A FTIR gas analyzer is also commercially available, such as the TITAN FTIR gas analysis system manufactured by MIDAC Corporation, of 130 McCormick Avenue, Costa Mesa, Calif. 92626.

BRIEF SUMMARY OF THE INVENTION

With parenthetical reference to the corresponding parts, portions or surfaces of the disclosed embodiment, merely for the purposes of illustration and not by way of limitation, the present invention provides an improved apparatus for sensing exhaust emissions (15) comprising a passive induction sampler (50) configured to sample exhaust from a source (16), a processing unit (30) connected to the induction sampler and configured to be mounted in close proximity to exhaust from the source, the processing unit comprising an input port (31) adapted to receive flow from the passive induction sampler, an output port (32), a flow path (33) between the input port and the output port, a sensor (34) for sensing one or more pollutants in the flow path, a processor (37) configured to receive measurements from the sensor, a power source (39), and a wireless transmitter (36) connected to the processor.

The source may comprise a combustion engine (18). The source may comprise an exhaust pipe (19) and the passive induction sampler may comprise an induction tube (51) extending from the input port of the processing unit into the exhaust pipe. The passive induction sampler may further comprise a valve (81) configured to control exhaust flow in the exhaust pipe. The induction tube may also comprise a bypass (82).

The source may comprise an exhaust pipe and the processing unit may be configured to be mounted to the exhaust pipe. The processing unit may be configured to be temporarily mounted to the exhaust pipe.

The source may be a stationary source selected from a group consisting of generators, drainage and irrigation pumps, and compressors. The source may be a mobile source selected from a group consisting of passenger cars, light trucks, large trucks, buses, motorcycles, off-road recreational vehicles, farm equipment, construction equipment, lawn and garden equipment, marine engines, aircraft, locomotives and water vessels.

The exhaust sensor may be selected from a group consisting of a non-dispersive infrared exhaust analyzer, a non-dispersive ultra-violet gas analyzer, and a chemical sensor. The processing unit may further comprise a flow meter (35) configured to measure flow in the flow path, and the flow meter may be selected from a group consisting of a turbine flow meter, an optical flow meter, a pressure flow meter and a thermal flow meter. The processor may comprise a microprocessor programmed to provide emission data as a function of measurements from the sensor and the flow meter. The pollutant may be selected from a group consisting of nitrogen oxides ($NO_x$), carbon monoxides (CO), carbon dioxides ($CO_2$), hydrocarbons (HC), sulfur oxides ($SO_x$), particulate matter (PM) and volatile organic compounds (VOCs).

The power source may comprise a nickel-metal hydride battery (39). The power source may further comprise a thermoelectric generator (38/75) connected to the battery and configured to recharge the battery. The power source may comprise a thermoelectric generator, the source may comprise an exhaust pipe, and the thermoelectric generator may comprise a thermoelectric sleeve (75) configured to attach to the exhaust pipe.

The system may further comprise a data relay module (40) comprising a receiver (41) configured to receive data transmitted wirelessly from the processing unit transmitter, an interface (21/44, 27/44) configured to receive performance data concerning the engine, and a transmitter (42) configured to wirelessly transmit data from the receiver and the interface. The performance data may be selected from a group consisting of engine rpm, intake manifold pressure, engine oil temperature, and intake air temperature, vehicle speed, and intake air mass flow. The interface may be connected to an engine control unit (17). The interface may comprise an engine rpm sensor (25), an engine pressure sensor (22) and an engine temperature sensor (23, 24).

The system may further comprise a data relay module comprising a receiver configured to receive data transmitted wirelessly from the transmitter, an interface configured to receive performance data concerning the engine, and a storage device (45) configured to store data from the receiver and the interface.

The source may comprise an exhaust pipe and the system may further comprise an exhaust flow meter (70) configured to measure flow in the exhaust pipe, and the flow meter may be selected from a group consisting of an acoustic flow meter, an optical flow meter and a magnetic flow meter. The source may comprise an exhaust pipe and the system may further comprise an exhaust flow sensor system (61) configured to measure flow in the exhaust pipe, and the flow sensor system may be selected from a group consisting of an electrochemical, thermal generating or mechanically flow-motivated sensor system.

In another aspect the invention comprises a sampler (50) configured to sample exhaust from a source, a processing unit (30) connected to the induction sampler and configured to be mounted in close proximity to exhaust from the source, the processing unit comprising an input port (31) adapted to receive flow from the sampler, an output port (32), a flow path (33) between the input port and the output port, a sensor (34) for sensing one or more pollutants in the flow path, a processor (37) configured to receive measurements from the sensor, a power storage device (39), a thermoelectric generator (38), and a wireless transmitter (36).

Accordingly, an object of the present invention is to provide an improved emissions measuring system which is adapted to be used to determine real-world vehicle emissions.

Another object is to provide an improved system which is adapted for use on a wide variety of vehicles.

Another object is to provide an improved system which may be used on a vehicle without permanent modification to the vehicle.

Another object is to provide an improved mass emissions measuring system which may be used without displacing a vehicle from service.

BRIEF DESCRIPTION OF THE DRAWINGS

FIG. 11 is a detailed schematic of an alternative embodiment of the induction sampler shown in FIG. 5.

DESCRIPTION OF THE PREFERRED EMBODIMENTS

Figure 1:
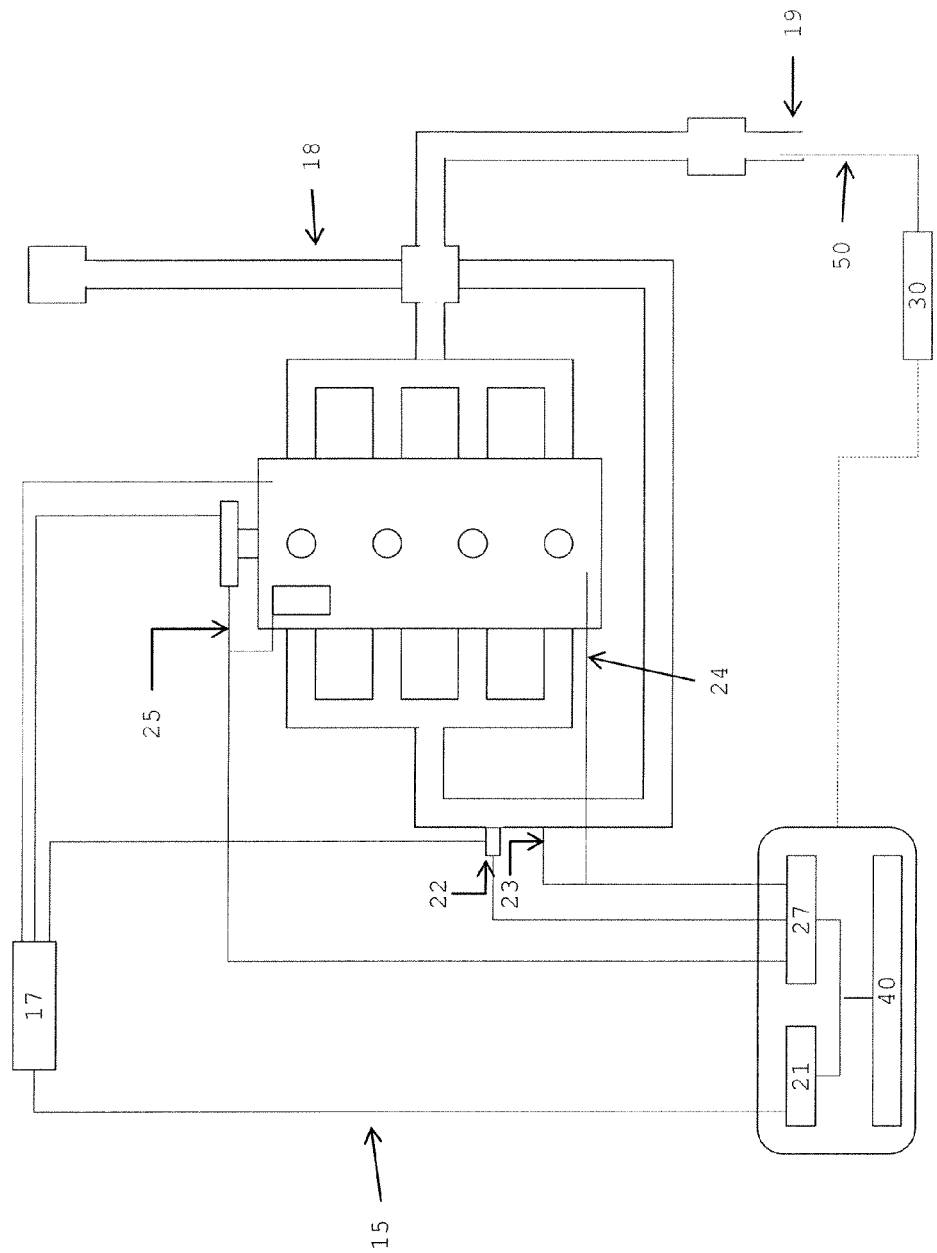
FIG. 1 is a schematic of a first embodiment of the improved emissions measuring system.

At the outset, it should be clearly understood that like reference numerals are intended to identify the same structural elements, portions or surfaces consistently throughout the several drawing figures, as such elements, portions or surfaces may be further described or explained by the entire written specification, of which this detailed description is an integral part. Unless otherwise indicated, the drawings are intended to be read (e.g., cross-hatching, arrangement of parts, proportion, debris, etc.) together with the specification, and are to be considered a portion of the entire written description of this invention. As used in the following description, the terms "horizontal", "vertical", "left", "right", "up" and "down", as well as adjectival and adverbial derivatives thereof, (e.g., "horizontally", "rightwardly", "upwardly", etc.), simply refer to the orientation of the illustrated structure as the particular drawing figure faces the reader. Similarly, the terms "inwardly" and "outwardly" generally refer to the orientation of a surface relative to its axis of elongation, or of rotation, as appropriate.

Referring now to the drawings, and more particularly to FIG. 1 thereof, this invention provides an improved emissions measuring system, of which the presently preferred embodiment is generally indicated at 15. System 15 is shown as broadly including passive induction sampler 50, exhaust processing unit 30, data relay 40, engine performance sensors 25, 22, 23 and 24 for sensing run-time parameters of engine 18, sensor data acquisition interface 27, and engine control interface 21.

Figure 5:
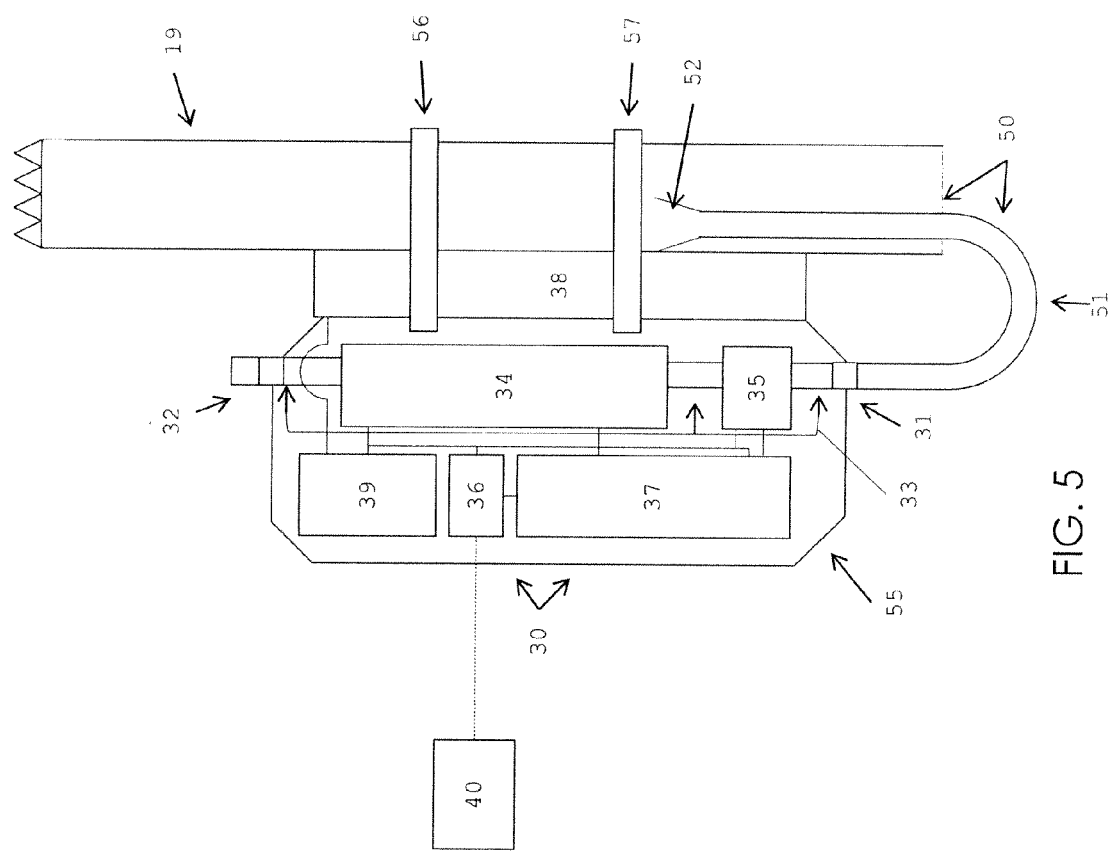
FIG. 5 is a detailed schematic of the processing unit shown in FIG. 1 mounted to a vehicle.

As shown in FIG. 5, passive induction sampler 50 is configured to sample exhaust from tailpipe 19. The exhaust sample is taken for analysis by diverting a portion of the exhaust flow in pipe 19 to processing unit 30 through partial occlusion of the normal exhaust system. Sampler 50 includes small-diameter fixed induction tube 51 that is inserted into tailpipe 19 and includes a widened frusto-conical exhaust collection end 52. Samples of the exhaust gases in tailpipe 19 are passively routed by sampler 50 to unit 30, where the sample's flow properties are measured and utilized to provide accurate pollutant measurements for the exhaust of vehicle 16. Passive induction sampler 50 conveys exhaust to processing unit 30 without the use of pumps.

As shown in FIG. 11, flow through sampler 50 may be controlled using valve 81 mounted on the end of tailpipe 19. Valve 81 is configured to partially or fully restrict the flow of exhaust gases from vehicle exhaust pipe 19 before they are exhausted into the ambient environment in order to facilitate a steady amount of sampled exhaust to processing unit 30. In this embodiment, valve 81 may be hinged and spring loaded or actuator controlled by processor 37. Sampled flow may be further controlled within passive flow sampler 50 with bypass outlet 83. The flow path within passive flow sampler induction tube 51 may be split with one path leading to emissions analyzing unit 30 and one path 83 leading to the ambient environment. Path 83 to the environment may control the flow through use of a static or dynamic flow control method. A static method may include use of a stationary restrictor, and a dynamic method, as shown in FIG. 11, may include use of valve 82 controlled mechanically or with an actuator connected to processor 37.

As shown in FIG. 5, exhaust processing unit 30 broadly includes input port 31 configured to receive flow from induction sampler 50, output port 32, flow path 33 between input port 31 and output port 32, gas analyzer 34 for measuring one or more pollutants in flow path 33, flow meter 35 for providing flow rate information, microprocessor 37 configured to receive measurements from analyzer 34 and flow meter 35, thermo-electric generator 38 connected to battery 39, and wireless transmitter 36 connected to microprocessor 37.

As shown, generator 38, battery 39, flow meter 35, analyzer 34, microprocessor 37 and transmitter 36 are contained in unitary housing 55 that is attached directly to tailpipe 19 of vehicle 16. In this embodiment, housing 55 includes two straps 56, 57 sized to extend around the outer perimeter of tailpipe 19. Straps 56 and 57 are tightened to mount processing unit 30 to tailpipe 19 with induction tube 51 extending in the appropriate manner into the exhaust stream of tailpipe 19.

As shown, sampled exhaust flows through induction tube 51 and input port 31 into processing unit 30. Flow meter 35 and gas analyzer 34 are positioned in flow path 33 between input port 31 and output port 32 to measure pollutants in the sampled exhaust. In this embodiment, gas analyzer 34 is a five-gas non-dispersive infra-red (NDIR) exhaust analyzer, which provides near real-time readings of concentrations of HC, CO, $CO_2$, $NO_x$ and $O_2$. Analyzer 34 is powered by battery 39. The OTC RG-240 digital five-gas analyzer manufactured by OTC, of 655 Eisenhower Drive, Owatonna, Minn. 55060, may be employed in this embodiment.

Because exhaust is sampled passively, or without the use of a pump or the like, flow meter 35 is provided. In this embodiment, flow meter 35 is a thermal mass flow meter. The D6F-02A1-110 flow meter manufactured by OMRON of Kyoto, Japan may be used in this embodiment.

Depending on the pollutants to be measured, alternative or additional analyzers may be employed. For example, for natural gas powered vehicles, and/or where methane and non-methane hydrocarbons (NMHC) are to be measured separately, several analyzer options exist. First, a hand-held methane/low-range CO NDIR analyzer may be added to the system. From a known concentration of methane and a known (experimentally determined) response of the 5-gas analyzer to methane (ratio of detected to actual methane concentration), both methane and NMHC concentrations can be obtained. A second NDIR unit with different response to methane may also be added. The methane and NMHC concentrations are then obtained from the two different HC readings by each analyzer. A portable flame ionization detector (FID) may be added to measure total hydrocarbons (THC). From the known response of the NDIR analyzer to methane, and HC and THC readings, both methane and NMHC emissions can be determined.

Alternatively or in addition, a particulate matter (PM) analyzer may be used. The PM-Trac analyzer manufactured by EmiSense, Inc., of 4205 West 1980, South Salt Lake City, Utah 84104, may be used in this embodiment. This sensor can be used to detect particulate matter in the exhaust stream and has an output signal which can be correlated to the PM concentration.

Other sensors or additional sensors that detect NOx, SOx and hydrocarbons can be utilized. Thus, a wide variety of gas, particulate or other sensors or analyzers may be included in unit 30 and introduced into the sampled exhaust flow. Constraints on sensor selection include accuracy, repeatability, sensitivity and temperature and humidity operating capabilities.

Different calibrating elements may be included depending on the pollutant being analyzed and the parameters and operating requirements of the subject analyzer or sensor, and such calibrating element may be either internal or external to the subject analyzer. For example, temperature, pressure, relative humidity or flow rate of the exhaust in flow path 33 may be sensed for calibration or other purposes. With respect to temperature, a conventional thermocouple may be used. For pressure, a conventional pressure transducer may be used, such as the PX138 transducer manufactured by Omega Engineering, Inc., of One Omega Drive, Stamford, Conn. 06907-0047. For humidity, a H1H-4000-02 humidity sensor, manufactured by Honeywell International Inc., of 101 Columbia Road, Morristown, N.J. 07962, may be used. An orifice flow meter utilizing temperature, pressure and humidity, a flow-restrictor and a second pressure transducer for measuring differential pressure across the flow restrictor may be used as an alternative to determine flow rate with thermal mass flow meter 35. In addition, a flow controller may be used to control the exhaust flow rate in flow path 33. For example, an electronically controlled proportional valve may be used.

In this embodiment, microprocessor 37 is a conventional onboard chip that controls and combines the flow, heat, recharge and communications data, as well as ensures a continuous second-by-second stream of information to engine data relay module 40. Microprocessor 37 collects data from analyzer 34 and flow meter 35 and communicates that data wirelessly through transmitter 36 to relay 40.

In this embodiment, battery 39 is a nickel-metal hydride battery. It stores power and buffers the power requirements of unit 30. Battery 39 includes a cathode of nickel-hydroxide, an anode of hydrogen absorbing alloys and a potassium-hydroxide electrolyte. The advantage of this type of battery is that it has a high energy density, can be deep cycled, has low internal impedance, has a flat discharge characteristic, has a broad operating temperature range, and has a rapid charge rate. The broad operating temperature range is important because of the proximity to tailpipe 19 and the expected heat generated during operating conditions of vehicle 16.

To augment the power supply, a self-contained renewable power generator is used to continuously recharge embedded battery 39. In this embodiment a conventional thermo-electric generator 38 is used. Processing unit 30 takes advantage of its proximity to excess heat released from exhaust in pipe 19 to generate additional power. In the embodiment shown in FIG. 5, thermo-electric generator 38 converts the heat energy from vehicle exhaust into electricity utilizing a thermocouple sandwiched between two aluminum conductors. A Seebec Effect occurs when a temperature gradient is applied to a conductor and produces an electromotive force as a function of the temperature differential applied. The magnitude of the electromotive force is a function of the temperature differential applied. This type of thermo-electric generator has the advantage of having no moving parts and being generally silent. The 1261G-7L31 thermo-electric generator series manufactured by Custom Thermoelectric, Inc., of 11941 Industrial Park Road, STE 5, Bishopville, Md. 21813, may be used in this embodiment. Thus, thermal energy is converted to electrical energy via the 'thermoelectric' or 'Seebeck effect'. Waste heat produced from the exhaust of vehicle 16 is converted to a 'trickle charge' to recharge battery 39, which powers the components of processing unit 30.

Figure 6:
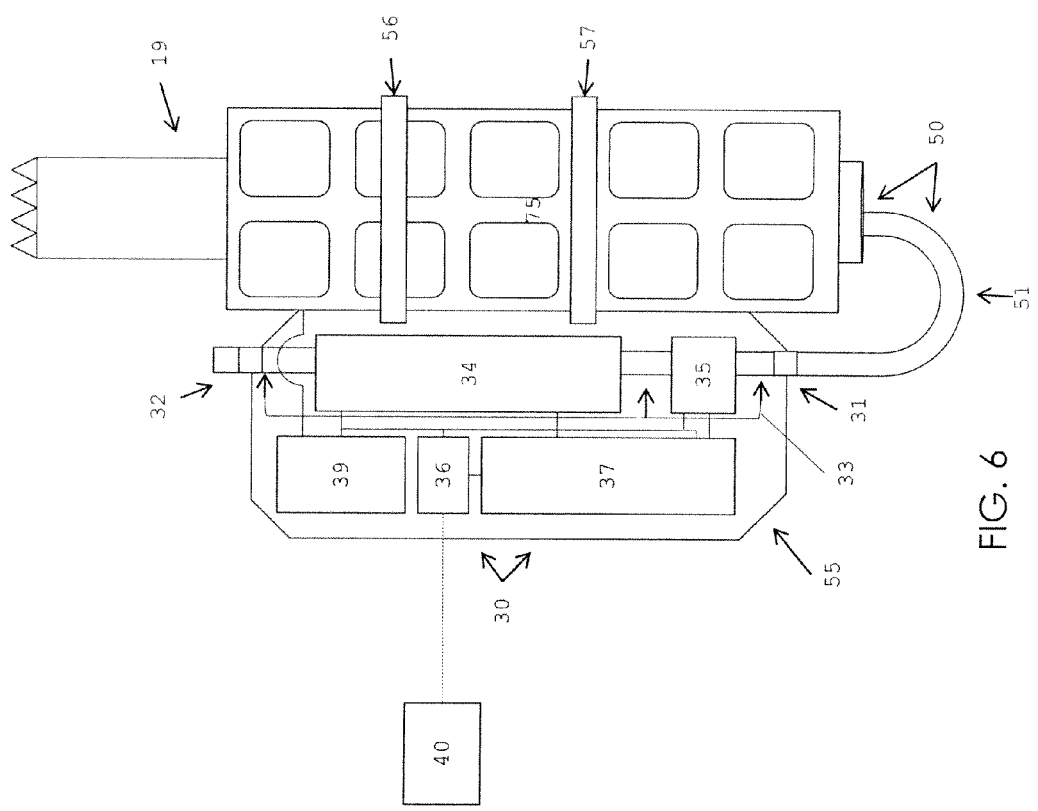
FIG. 6 is a detailed schematic of a first alternative embodiment of the processing unit shown in FIG. 5.

Alternatively, as shown in FIG. 6, thermal sleeve 75 may be used. Thermal sleeve 75 is formed of interconnected thermoelectric devices placed together in series around exhaust pipe 19. These devices are formed from multiple paired n-type semiconductors and p-type semiconductors sandwiched between a hot side ceramic plate and a cold side plate. For example, small thermoelectric devices of 40 mm by 40 mm can currently produce up to 2.8 volts, 1.05 amps and 3 watts. As shown in FIG. 6, unit 30 and power generation sleeve 75 are connected directly to tailpipe 19 with standard automotive hose clamps 56 and 57. Thus, in this embodiment thermoelectric devices surround the entire tailpipe cylinder 19 to create a sleeve of thermoelectric generation 75.

Alternatively or in addition, thermoelectric devices may be connected to the engine manifold to produce the needed voltage, amperage and watts to meet the power requirements of the system. As a secondary power source, a solar collector, configured in a similar fashion or in parallel, may be included to augment the power requirements of the system.

In this embodiment, transmitter 36 is a Bluetooth wireless transmitter. This affords good data transmission rates and the ability to ensure such data transmissions are properly encrypted and secure. The BlueSentry Bluetooth Data Acquisition Module, part number RN-800S-CB, manufacture by Roving Networks, Inc., of 809 University Avenue, Los Gatos, Calif. 95032, which supports eight (8) sixteen bit (16-bit) data input channels and samples data at rates up to 3,000 times per second, may be used in this embodiment. Alternatively, transmitter 36 may be a IEEE 802.11x WiFi data communication device. In either case, the measurements from analyzer 34 are transmitted wirelessly, preferably in a real-time and continuous manner, to electronic data relay 40.

Figure 2:
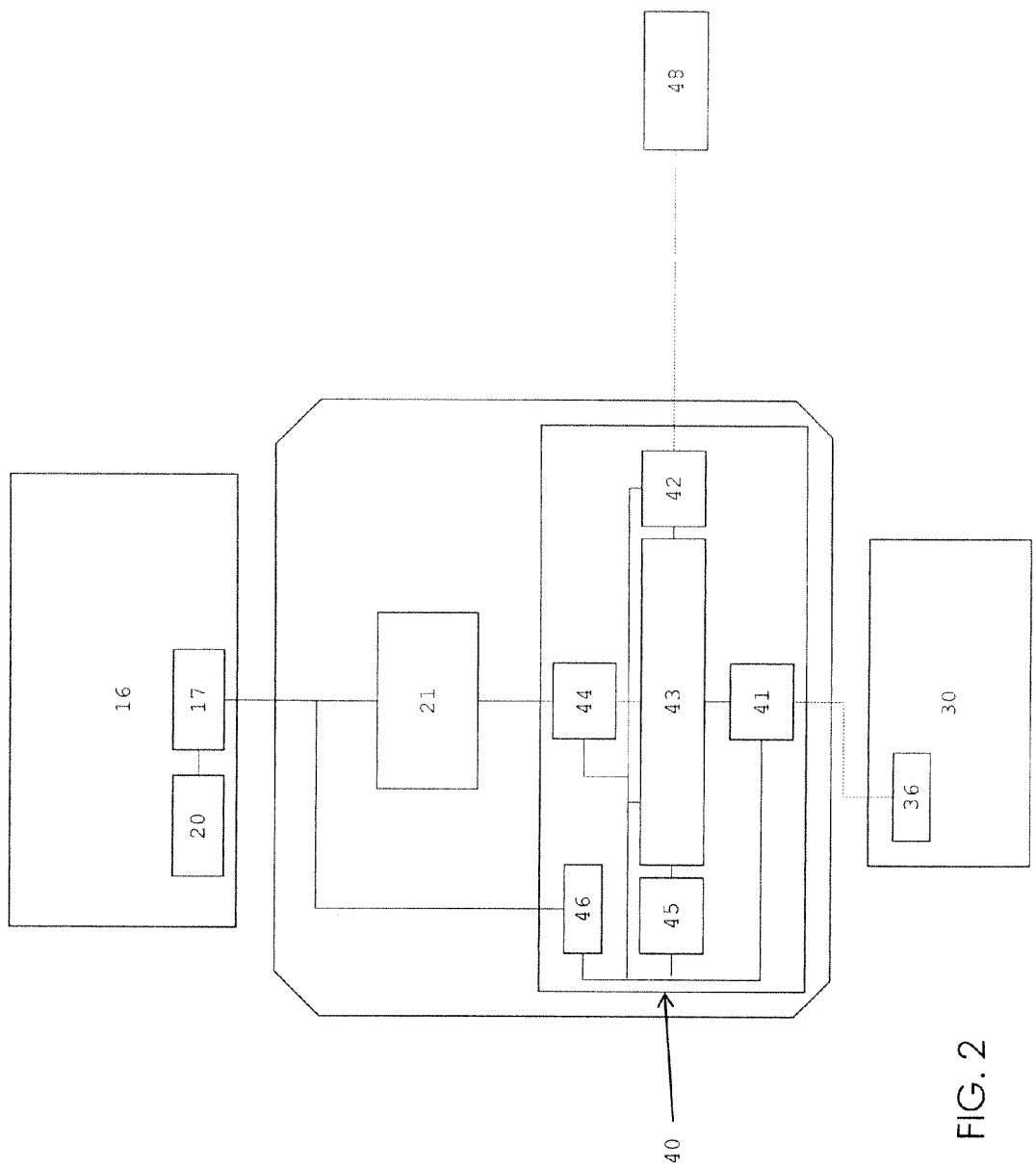
FIG. 2 is a detailed schematic of the data relay shown in FIG. 1 in a first configuration.

To compute mass flow rate of a particular pollutant, the mass flow rate of air through engine 18 needs to be known. In this embodiment, there are a number of ways to determine such airflow. As shown in FIG. 2, the first is through direct readings from engine 18 via an engine control interface 21 connected to engine control unit (ECU) 17 of engine 18. Some vehicles are manufactured with suitable on-board technology in the form of an engine control unit that monitors vehicle run-time parameters. In such vehicles, the system may be configured to obtain one or more desired run-time parameters directly from the engine control unit through control interface 21 without requiring use of additional engine performance sensors 25, 22, 23 and 24. Such parameters may include engine rpm, intake manifold pressure, engine oil temperature, vehicle speed, intake air temperature, intake air mass flow, and any additional parameters that may be reported by the vehicle ECU. Thus, on computer controlled engines where engine data can be obtained by an engine diagnostic link, intake air flow or fuel flow is computed from the engine data obtained by engine control interface 21 from vehicle ECU 17.

Because modern computer-controlled engines provide operating data such as vehicle speed, engine rpm, intake air and coolant temperature, intake air pressure, intake air mass flow, throttle position and engine load through the engine control unit, this information can be fed to processor 43 by engine control interface 21. The Pro-Link 9000 scan tool with heavy-duty cartridge manufactured by Microprocessor Systems Inc., of Sterling Heights, Mich., may be employed in this embodiment. Alternatively, the Snap-On MT-2500 engine diagnostic scanner manufactured by Snap-On Diagnostics, of Kenosha, Wis. 53141-1410, may be employed. As another alternative, the DPA3 engine computer interface manufactured by Dearborn Group, of 27007 Hills Tech Court, Farmington Hills, Mich. 48331, which supports the SAE J1708 and J1939 and other relevant vehicle data interface standards, may be used. Thus, system 15 may obtain vehicle run-time parameters directly from vehicle ECU 17 and engine control interface 21 in lieu of using one or more engine performance sensors 25, 22, 23 and 24.

Figure 3:
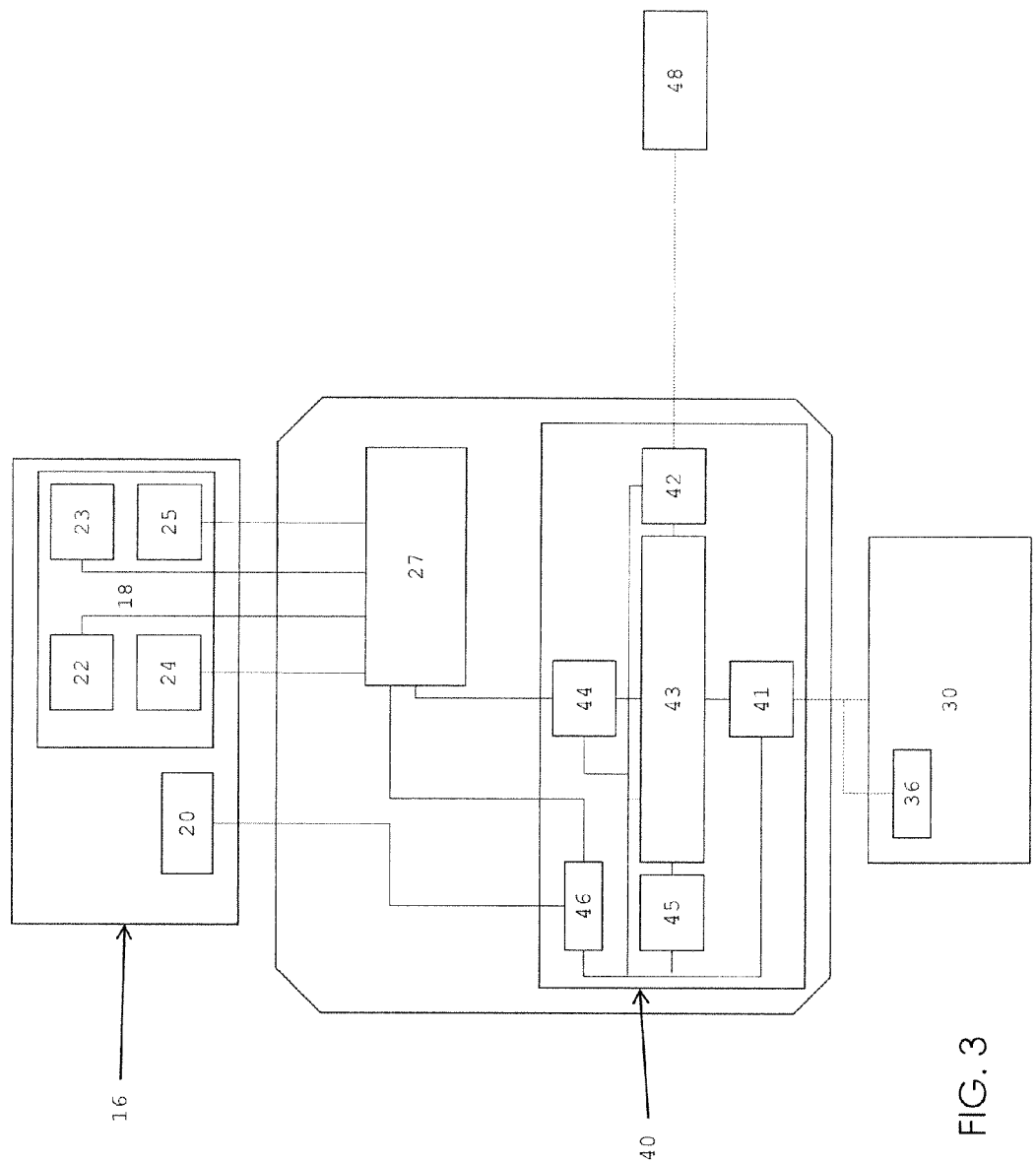
FIG. 3 is a detailed schematic of the data relay shown in FIG. 1 in a second configuration.

As shown in FIG. 3, in cases where there is no engine control interface 21 or in engines that are not computer controlled, sensors 25, 22, 23 and 24 may be attached directly to engine 18. Engine rpm, intake manifold pressure, intake oil temperature and intake air temperature are measured using engine rpm sensor 25, intake manifold pressure sensor 22, intake oil temperature sensor 24, and intake air temperature sensor 23. Sensors 25, 22, 23 and 24 are adapted to be temporarily mounted to the engine during testing.

Intake oil temperature sensor 24 is a conventional dipstick temperature probe which is inserted in place of the oil dipstick. Engine rpm sensor 25 is a standard rpm pickup probe, which is adapted to clamp onto one of the engine's spark-plug wires. The dipstick temperature probe and rpm inductive clamp manufactured by OTC, a division of SPX Corporation, of Owatonna, Minn. 55060-1171, may be employed in this embodiment. Alternatively, engine rpm sensor 25 maybe a phototachometer used with the shaft or other rotating part of engine 18. A light source and a light detector are positioned such that each time the rotating part completes a full turn, the light hits and is reflected from the reflective surface on the rotating engine part and is detected by the detector.

Manifold pressure sensor 22 is a manifold absolute pressure transducer which is connected to the intake air manifold of the engine and senses the manifold absolute pressure in the manifold. On turbocharged engines, pressure sensor 22 is placed downstream of the turbocharger. Alternatively, manifold pressure sensor 22 may be a pressure sensor added to an existing engine vacuum line. The pressure sensor is adapted to take readings from the engine's timing advance line. A T-adaptor is inserted in the vacuum line and connected to a pressure transducer. The pressure transducer includes a link to processor 43 such that the manifold pressure or vacuum may be recorded and stored.

Intake air temperature sensor 23 is connected in a similar position to manifold pressure sensor 22. Intake air temperature sensor 23 is a conventional temperature measuring device which is capable of sensing intake air temperature.

Data acquisition interface 27 is a conventional AD converter which converts analogue input from the engine sensors to digital output. Also, if other parameters not available from an engine control interface 21 are required, than engine performance sensors 25, 22, 23 and 24 or other sensors may be employed for obtaining such data.

Figure 4:
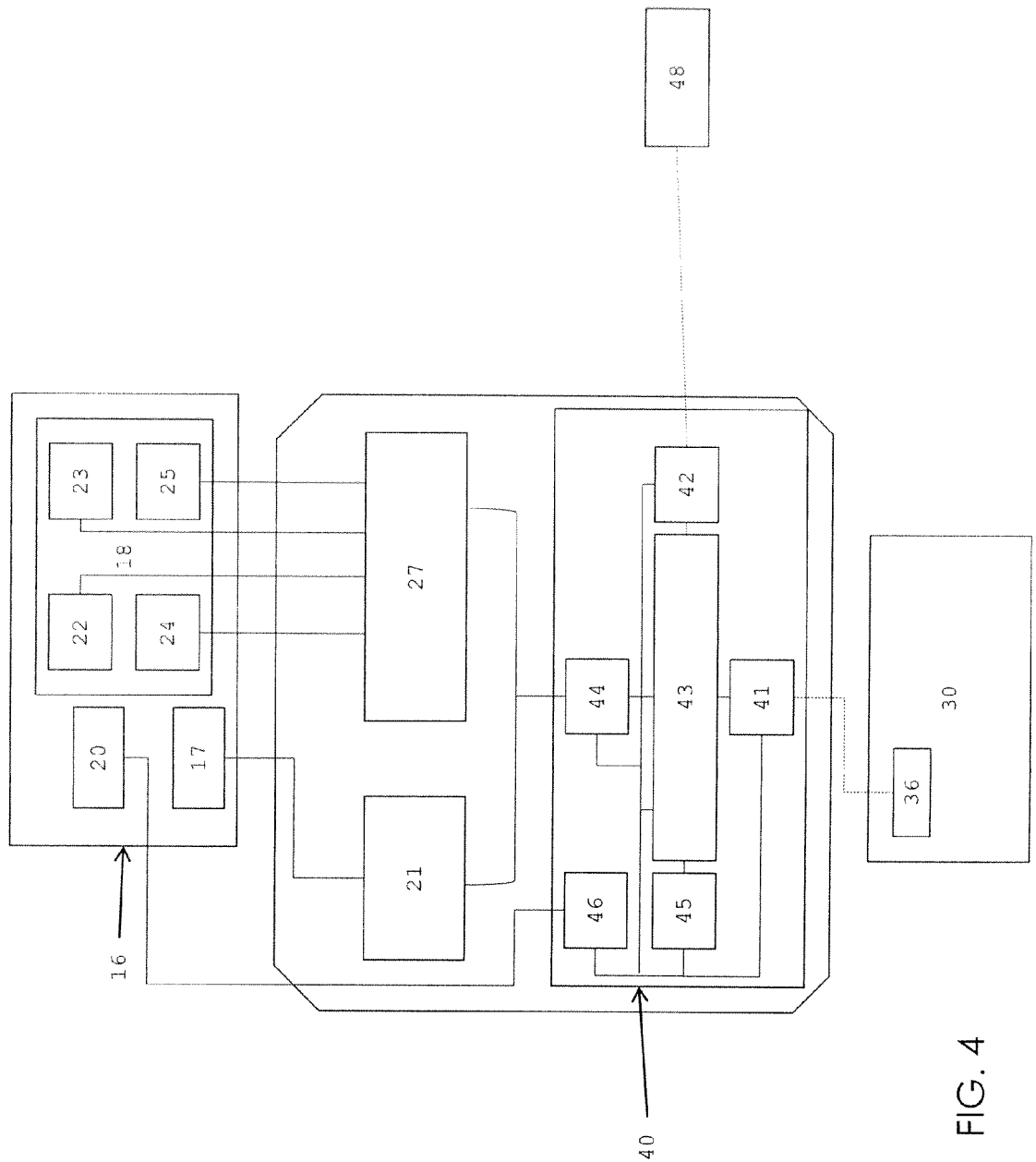
FIG. 4 is a detailed schematic of the data relay shown in FIG. 1 in a third dual configuration.

As shown in FIG. 4, data relay 40 is also configured to be used in combination with both engine ECU 17 and one or more independent sensors 22-25 when one or more additional independent sensor measurements may be needed or desired.

Figure 7:
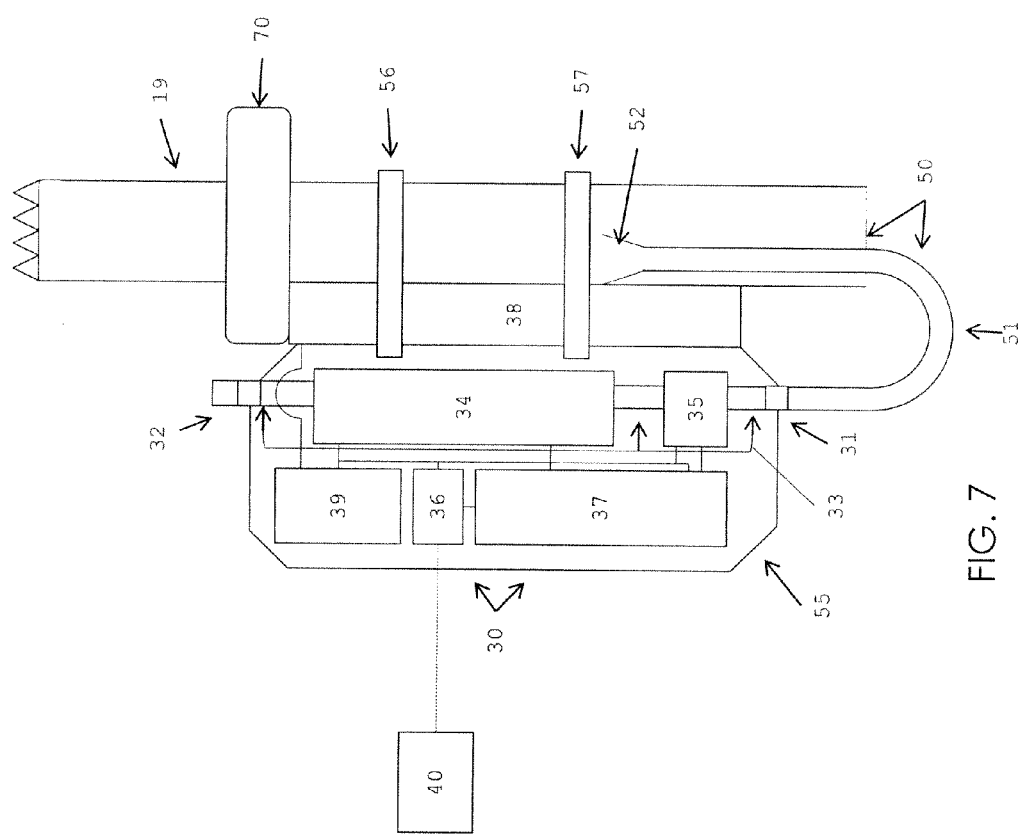
FIG. 7 is a detailed schematic of the embodiment of the processing unit shown in FIG. 5 with an additional vehicle exhaust flow measuring system.
Figure 8:
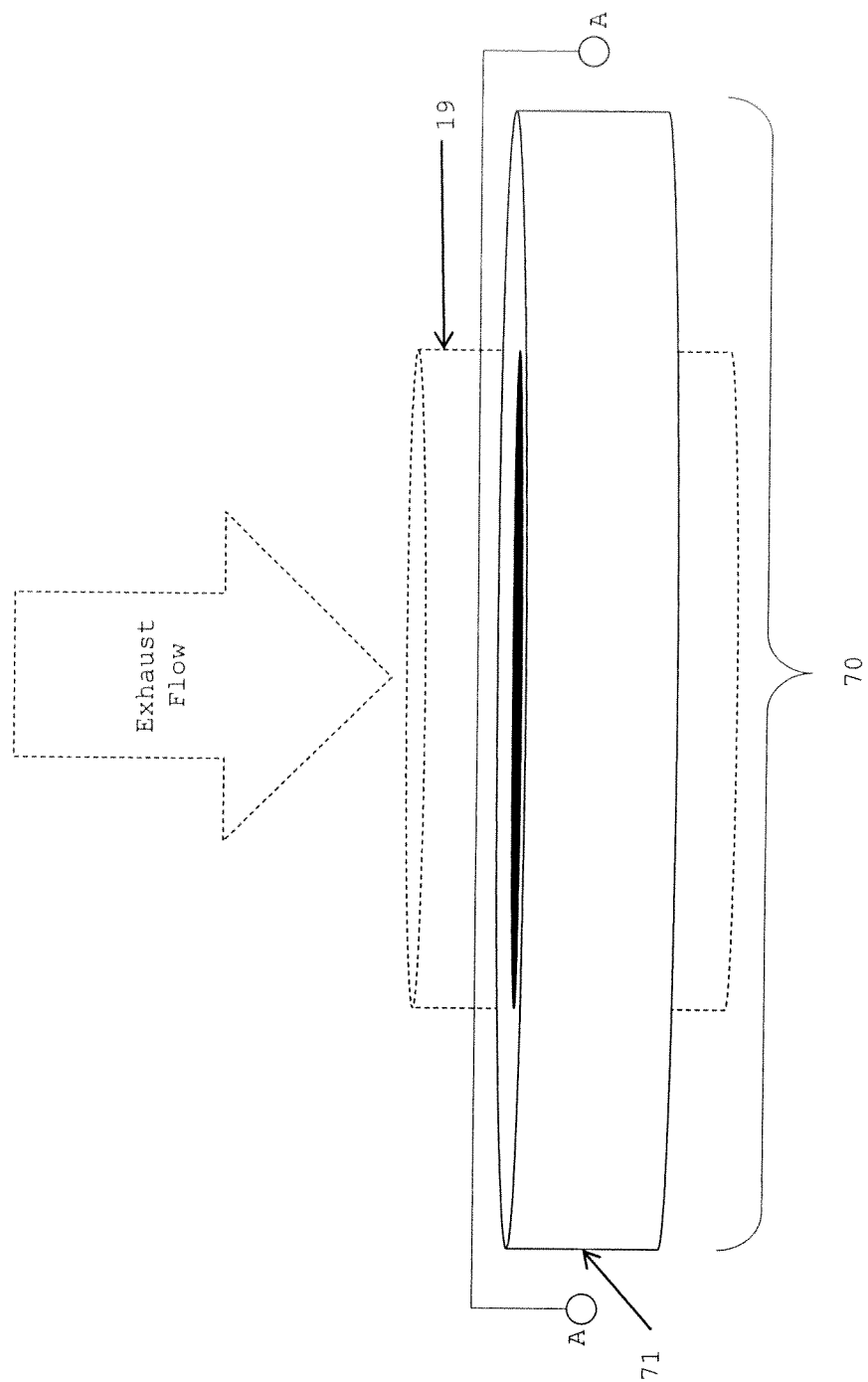
FIG. 8 is a top perspective view of the vehicle exhaust flow measuring system shown in FIG. 7.
Figure 9:
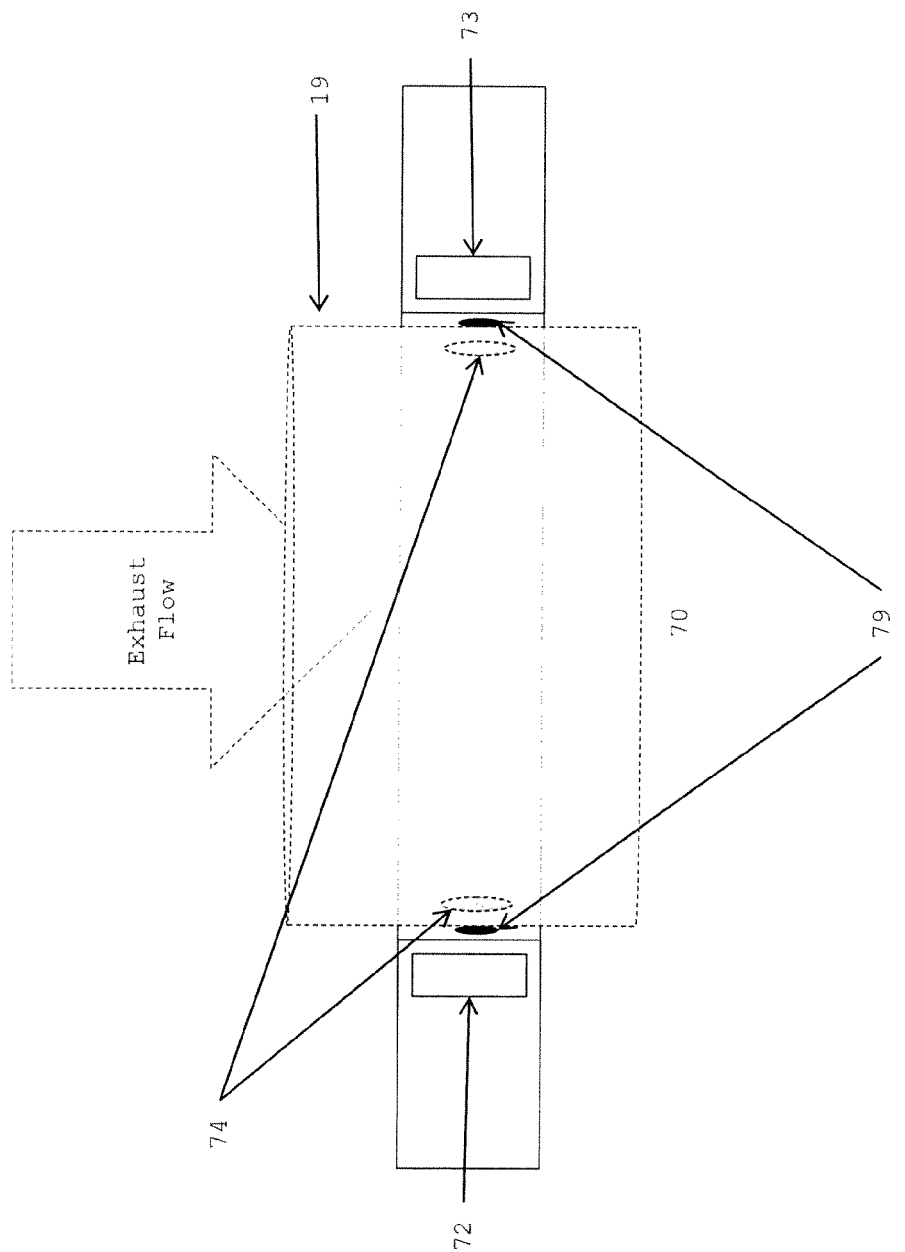
FIG. 9 is a vertical cross-sectional view of the vehicle exhaust flow measuring system shown in FIG. 8, taken generally on line A-A of FIG. 8.

FIGS. 7-9 show an embodiment with a direct exhaust flow measurement device 70 added. With flow meter 70, mass flow rate from interface 21 and/or 27 can be supplemented or checked for accuracy in the computation of mass flow rate. Exhaust flow measurement device 70 may be an optical, acoustical or magnetic flow measurement device. As shown, device 70 comprises a cylindrical ring or sleeve 71 that fits around the outside of tailpipe 19 just upstream of thermoelectric generator 38. Apertures 74 are provided through tailpipe 19 and, in this optical embodiment, light is directed transversely across the gas or particulate exhaust direction of flow through tailpipe 19. Light transmitting element 72 is provided on one side of housing 71 and light receiving element 73 is provided on the opposite side. Receiving element 73 may be a mirror, diode, photo-resistor or other type of light receiver. Light is transmitted from transmitter 72 through apertures 79 in housing 71 and correspondingly provided apertures 74 in exhaust pipe 19 to receiver 73. The flow rate is measured by sensing the velocity of microscopic particulates naturally occurring in the exhaust.

The acoustical embodiment is similar but utilizes an acoustic wave emulator and an acoustic wave receiver. The acoustic velocimetry is designed to measure, record and transmit the speed of gas flow particles and particulate matter by sending a relatively high frequency signal directed perpendicular to the gas flow. The measurement is performed as the acoustic wave is adjusted and directed differently than the predicted acoustic wave path. The acoustic wave encounters the receiver and the shift is used in calculation of mass flow.

The magnetic, ionization, or electric field embodiment employs a device that magnetizes or ionizes particles in the gas flow. These ions then generate a voltage when traveling through the magnetic field applied through the device. The amount of voltage generated gives rise to an indication of the speed of the gas flow.

Figure 10:
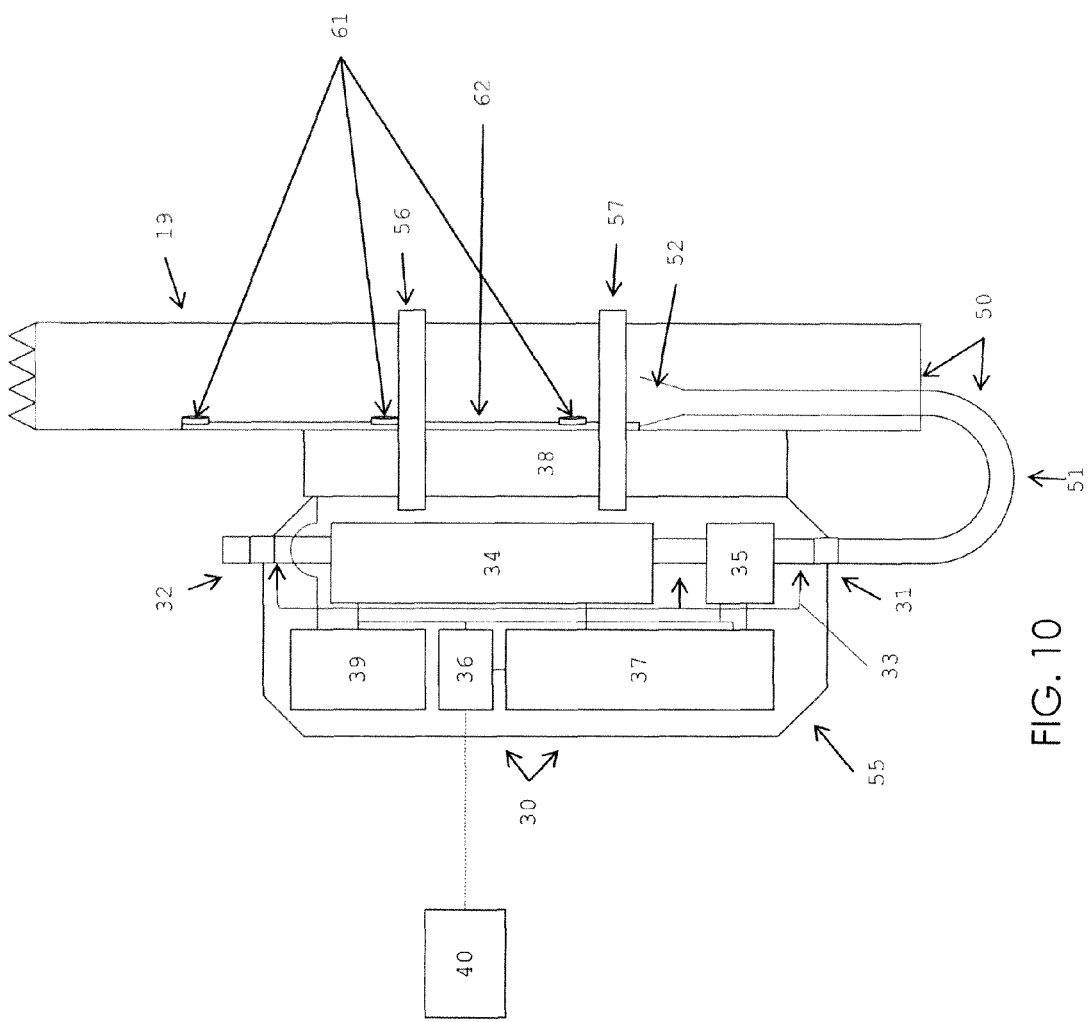
FIG. 10 is a detailed schematic of an alternative embodiment of the vehicle exhaust flow measuring system shown in FIG. 7.

FIG. 10 shows an alternative embodiment of an added exhaust flow measurement device 62. In this embodiment multiple sensors 61 are spaced longitudinally at selected locations along the inner surface of pipe 19. As gas flows by each of sensors 61 a signal is generated through the use of several different sensor approaches. Sensors 61 may be, for example, conventional electrochemical, thermal generating, or mechanically flow-motivated sensors.

In this embodiment, flow rate device 70 or 61 is connected to processing unit 30 and readings are communicated to processor 37 and in turn to relay 40. Flow rate device 70 or 61 are powered by battery 39.

As shown in FIGS. 2-4, data relay 40 generally includes receiver 41 for receiving wireless transmissions from transmitter 36, computer interface 44 in communication with engine control interface 21 and/or engine sensor data interface 27, central processor unit 43, data storage 45, transceiver 42, and power connection 46.

Relay 40 may be temporarily or permanently mounted on vehicle 16 and is preferably secured against tampering through the use of suitable security measures such as strong username/password combinations, strong encryption on all networking interfaces, and a hardened physical enclosure. Relay 40 continually monitors one or more engine performance parameters and the emission data from unit 30, including flow rate data from device 70 or 61 if desired, stores this data locally in permanent, non-volatile memory 45, and then relays the data via transmitter 42 to a remote data repository or CPU 48 through some intervening medium such as a cellular phone network, a wireless local area network, and/or the internet. Relay 40 creates one record of data every second containing all captured data, with related "housekeeping" information for keeping track of such data.

In the configuration shown in FIG. 2, relay 40 is powered through a power connection 46 to vehicle ECU 17, which is in turned powered by the battery 20 of vehicle 16. In the configurations shown in FIGS. 3 and 4, relay 40 is powered directly by the battery 20 of vehicle 16 through, for example, a direct fused cable connected to power connection 46.

In this embodiment, receiver 41 is a conventional Bluetooth receiver for receiving wireless transmissions from transmitter 36. The RN-41 manufactured by Roving Networks, of 809 University Avenue, Los Gatos, Calif. 95032, may be used in this embodiment.

Electronic computer interface 44 houses the data acquisition ports (analog and serial) that allow relay processor 43 to communicate with engine control interface 21 and sensor data interface 27. Electronic computer interface 44 is built into relay processor 43. The basic components of this module include an analog and serial input connection with capabilities of sending data to transmitter 42 for relay to exhaust processing unit 30.

Measurements or data from unit 30, including if desired flow rate data from device 70 or 61, and the required parameters of engine 18, whether obtained from engine control interface 21 or from discrete permanently or temporarily attached engine sensors 25, 22, 23 and 24 and engine sensor data interface 27, are processed by processor 43. In this embodiment, processor 43 may be an Ep301v manufactured by Toronto MicroElectronics of 6185 Danville Road, Mississauga, Ontario L5T 2H7, Canada. Processor 43 executes software to receive all incoming data from unit 30 and engine sensor data interface 27 (sensors 25, 22, 23 and/or 24) and/or engine control interface 21. The data may be tagged with user input information, such as vehicle identification data and driver identification data, for future reference. Upon processing, emissions data is stored in permanent, non-volatile memory device 45. The MicroSD 4 GB memory card, part number P-SDU4GB4-SF, manufactured by PNY, Inc. of 299 Webro Rd., Parsippany, N.J. 07054, may be used in this embodiment.

In this embodiment, transceiver 42 is a cellular wireless transceiver or an IEEE 802.11x wireless transceiver. From relay 40, emissions, engine run-time parameters and/or computed measurements are transmitted, preferably in a real-time and continuous manner, through a cellular network or other intervening data transmission medium, to remote CPU 48.

In this embodiment, processor 43 is programmed to use the received data to compute exhaust mass air flow which, when multiplied by the measured concentrations of pollutants in the exhaust gas, may be used to provide emissions data in grams per second, which is the industry standard for vehicle mass emissions. Additional computations could be employed to provide, for example, second-by-second and total grams per gallon and grams per mile emissions data. In the event of lost or otherwise dropped data, linear interpolation can optionally be performed to fill in the missing data provided such missing data does not exceed a predetermined number of consecutive missed samples, such as, for example, 3 samples. In the event that more than 3 samples are missed consecutively, an error condition may be indicated and user intervention may be required to investigate the cause of the error. Relay 40 can relay this error state to the vehicle user and/or remote CPU 48.

To determine the concentration of pollutants such as hydrocarbons (HC), carbon monoxide (CO), nitrogen oxides ($NO_x$), carbon dioxide ($CO_2$) and oxygen ($O_2$) in the exhaust of engine 18, the exhaust gas is sampled from tailpipe 19 by sampler 50 and analyzed by unit 30. In-line filters may be located before analyzer 34 to remove water and particulate matter from the sample. The filters may include a pre-filter to remove large diesel exhaust particles, a coarse filter, and a fine 0.01 mm coalescing filter that removes heavy aerosols and most of the water vapor. The measurements from analyzer 34 are then used to determine the concentrations. A number of methods for such determinations are known. For example, U.S. Pat. No. 6,308,130, entitled "Portable On-Board Mass Emissions Measuring System," discloses a method for determining mass emissions. U.S. Pat. No. 6,435,019, entitled "Portable On-Board System for Measuring Vehicle Exhaust Particulate Emissions," discloses a method of determining emissions of particulate matter. The disclosure of each of U.S. Pat. No. 6,308,130 and U.S. Pat. No. 6,435,019 are incorporated in their entirety herein by reference.

Processor 43 is programmed to synchronize the data received. Sensors 22-25 and/or vehicle ECU 17, flow meter 34, flow measuring devices 70 and 61, and exhaust analyzer 34 produce data with a certain delay (or response time), at a certain rate, and with gaps. Both the delay and the rate can be obtained from the instrument manufacturer and/or obtained experimentally. The gaps are caused by equipment malfunction or by events, such as periodic zeroing of exhaust analyzer 34.

On each set of data, the delay is subtracted from the time stamp. Linear interpolation is then used to generate one record every second (or other set time interval). Small gaps (usually less than 3 seconds) in the data are filled using the linear interpolation. If a large gap exists, the data is marked as "missing". All data is then combined into one set, which includes vehicle speed and engine operating parameters, such as intake/fuel/exhaust flow, and exhaust concentrations. Processor 43 may be programmed to use this data for several purposes. First, mass emissions in grams/mile for the trip can be calculated by adding all grams/second data for the trip, and dividing by the total distance. The total distance is obtained by adding vehicle speed data in miles per second for the trip, excluding the sections during which there is "missing data". (Miles/second=miles/hour÷3600). If the speed data is not available, the distance can be obtained from the vehicle odometer. Second, real-time mass emissions in grams/mile can be calculated by dividing grams/second emissions by instantaneous vehicle speed in miles/second. Third, fuel consumption, both total and real-time, can be obtained by solving the set of equations for fuel flow in moles/second, and multiplying the results by the fuel molecular weight (for grams/second) and, when needed, by fuel density (for gallons/second data). Fourth, real-time mass emissions in grams/gallon can be obtained by dividing grams/second emissions by fuel flow. Fifth, total mass emissions in grams/gallon can be obtained either by integrating the real-time emissions data or by dividing the total emissions for the trip by the total fuel consumption for the trip.

Determination of emission concentrations and/or mass emissions using processor 43 within relay 40 allows for the instantaneous communication of such data with other on-board instruments and driver interfaces. This would find applicability in a permanent or semi-permanent installation of system 15 on vehicle 16.

Alternatively to programming processor 43 to perform the calculations described above, raw data may be relayed from relay 40 to remote CPU 48, which may include a processor for manipulating and processing the transmitted data. Determining emissions with such a remote processor decreases the functional requirements of relay 40. Relay 40 and/or remote CPU 48 may also include a user interface, such as a display and/or keyboard, for accessing the operating environment of system 15 and for displaying and manipulating the emissions data.

In this embodiment, data is relayed by transmitter 42 to remote CPU 48 using a cellular network. Ideally, cellular service is continuously available and data is relayed to the central data repository on a continuous, real-time basis. If cellular service is substandard, and connections thereto are only intermittent, relay 40 stores the data in storage device 45 and awaits a standard cellular connection and then transmits all data not yet transmitted since the last successful transmission up to and including the present data being collected and continues transmitting data as it is collected until the cellular network is no longer available. Relay 40 is preferably provided with a large permanent, non-volatile memory capacity capable of storing in excess of one week of collected data, so there will never be a circumstance where data is ever totally lost. Data may be captured at any suitable rate such as once per second, with much higher or lower sampling rates possible as limited by the maximum supported data rate of the sampling hardware.

For operation where there is no cellular service, data can alternatively be transmitted using IEEE 802.11x compliant wireless networking technology. In these environments, such as at shipping ports and construction sites, wireless 802.11x networks could be established to provide coverage such that the vehicles would be in communication with the data repository for data transmission before storage device 45 reaches its full capacity. Where neither cellular service nor 802.11x network capacity exists, periodic downloads of collected data could be accomplished by connecting relay 40 with a data collection device, such as a USB drive, PDA or laptop, to download all data since the last download.

Regardless of the manner in which data is ultimately relayed from relay 40 to CPU 48, relay 40 keeps track of what data has been transmitted and what data has not been transmitted and automatically knows where to resume each subsequent transmission or download. This may be accomplished by sequentially stamping each record with the date and time, by indexing or numbering each record of captured data with a sequence number and by keeping track of the last successfully transmitted sequence number for a given date. The sequence number may begin with the integer number one ("1") for the first sample taken in a given day, and then may be monotonically incremented by adding the integer number one ("1") to each preceding sequence number until midnight, after which the sequence number may be cycled back to the integer number one ("1") and the sequence numbering process is begun again. If the vehicle being monitored runs for 24 straight hours, 86,400 discrete samples would be collected and stored at one preferred data sampling rate, one for each second of a day. Given current memory technology, relay 40 should be capable of storing in excess of 4 million records in permanent, non-volatile storage device 45, corresponding to roughly 50 days of captured data. As memory technology improves or otherwise becomes more cost-effective, additional memory capacity may be added to increase the amount of data which can be stored in the local storage device. Once the local storage device has consumed all available allocated space for captured data, the oldest data may be overwritten in a "First-In, First-Out", or "FIFO", manner thereby ensuring that the most recent data is always available on the local storage device. Other conventional methods could be employed to achieve the same result.

Regardless of intervening transmission medium, data is preferably transmitted using strong end-to-end Strong Socket Layer (SSL) encryption technology to protect against data tampering, eavesdropping and message forgery. The SSL implementation may, for example, utilize a 128 bit cipher and is the industry standard encryption technology used for online banking and stock trading over the internet.

The present invention contemplates that many changes and modifications may be made. Therefore, while the presently-preferred form of the emissions measuring system has been shown and described, and several modifications and alternatives discussed, persons skilled in this art will readily appreciate that various additional changes and modifications may be made without departing from the spirit of the invention, as defined and differentiated by the following claims.

What is claimed is:

1. An apparatus for sensing exhaust emissions comprising:
a passive induction sampler configured to sample exhaust from a source;
a processing unit connected to said induction sampler and configured to be mounted in close proximity to exhaust from said source;
said processing unit comprising:
 (a) an input port adapted to receive flow from said passive induction sampler;
 (b) an output port;
 (c) a flow path between said input port and said output port;
 (d) a sensor for sensing one or more pollutants in said flow path;
 (e) a processor configured to receive measurements from said sensor;
 (f) a power source; and
 (g) a wireless transmitter connected to said processor.

2. The apparatus set forth in claim 1, wherein said source comprises a combustion engine.

3. The apparatus set forth in claim 1, wherein said source comprises an exhaust pipe and said passive induction sampler comprises an induction tube extending from said input port of said processing unit into said exhaust pipe.

4. The apparatus set forth in claim 3, wherein said passive induction sampler further comprises a valve configured to control exhaust flow in said exhaust pipe.

5. The apparatus set forth in claim 3, wherein said induction tube comprises a bypass.

6. The apparatus set forth in claim 1, wherein said source is a stationary source selected from a group consisting of generators, drainage and irrigation pumps, and compressors.

7. The apparatus set forth in claim 1, wherein said source is a mobile source selected from a group consisting of passenger cars, light trucks, large trucks, buses, motorcycles, off-road recreational vehicles, farm equipment, construction equipment, lawn and garden equipment, marine engines, aircraft, locomotives and water vessels.

8. The apparatus set forth in claim 1, wherein said source comprises an exhaust pipe and said processing unit is configured to be mounted to said exhaust pipe.

9. The apparatus set forth in claim 8, wherein said processing unit is configured to be temporarily mounted to said exhaust pipe.

10. The apparatus set forth in claim 1, wherein said sensor is selected from a group consisting of a non-dispersive infra-red exhaust analyzer, a non-dispersive ultra-violet gas analyzer, and a chemical sensor.

11. The apparatus set forth claim 1, wherein said processing unit further comprises a flow meter configured to measure flow in said flow path.

12. The apparatus set forth in claim 11, wherein said flow meter is selected from a group consisting of a turbine flow meter, an optical flow meter, a pressure flow meter and a thermal flowmeter.

13. The apparatus set forth in claim 11, wherein said processor comprises a microprocessor programmed to provide emission data as a function of measurements from said sensor and said flow meter.

14. The apparatus set forth in claim 1, wherein said power source comprises a nickel-metal hydride battery.

15. The apparatus set forth in claim 14, wherein said power source further comprises a thermoelectric generator connected to said battery and configured to recharge said battery.

16. The apparatus set forth in claim 1, wherein said power source comprises a thermoelectric generator.

17. The apparatus set forth in claim 16, wherein said source comprises an exhaust pipe and said thermoelectric generator comprises a thermoelectric sleeve configured to attach to said exhaust pipe.

18. The apparatus set forth in claim 1, wherein said pollutant is selected from a group consisting of nitrogen oxides ($NO_x$), carbon monoxides (CO), carbon dioxides ($CO_2$), hydrocarbons (HC), sulfur oxides ($SO_x$), particulate matter (PM) and volatile organic compounds (VOCs).

19. The apparatus set forth in claim 2, and further comprising a data relay module comprising:
 (a) a receiver configured to receive data transmitted wirelessly from said processing unit transmitter;
 (b) an interface configured to receive performance data concerning said engine; and
 (c) a transmitter configured to wirelessly transmit data.

20. The apparatus set forth in claim 19, wherein said performance data is selected from a group consisting of engine rpm, intake manifold pressure, engine oil temperature, intake air temperature, vehicle speed, and intake air mass flow.

21. The apparatus set forth in claim 19, wherein said interface is connected to an engine control unit.

22. The apparatus set forth in claim 19, wherein said interface comprises an engine rpm sensor, an engine pressure sensor and an engine temperature sensor.

23. The apparatus set forth in claim 2, and further comprising a data relay module comprising:
 (a) a receiver configured to receive data transmitted wirelessly from said processing unit transmitter;
 (b) an interface configured to receive performance data concerning said engine; and
 (c) a storage device configured to store data from said receiver and said interface.

24. The apparatus set forth in claim 1, wherein said source comprises an exhaust pipe and further comprising an exhaust flow meter configured to measure flow in said exhaust pipe.

25. The apparatus set forth in claim 24, wherein said flow meter is selected from a group consisting of an acoustic flow meter, an optical flow meter and a magnetic flow meter.

26. The apparatus set forth in claim 1, wherein said source comprises an exhaust pipe and further comprising an exhaust flow sensor system configured to measure flow in said exhaust pipe.

27. The apparatus set forth in claim 26, wherein and the flow sensor system is selected from a group consisting of an electrochemical, thermal generating or mechanically flow-motivated sensor system.

28. An apparatus for sensing exhaust emissions comprising:
a sampler configured to sample exhaust from a source;
a processing unit connected to said sampler and configured to be mounted in close proximity to exhaust from said source;

said processing unit comprising:
- (a) an input port adapted to receive flow from said sampler;
- (b) an output port;
- (c) a flow path between said input port and said output port;
- (d) a sensor for sensing one or more pollutants in said flow path;
- (e) a processor configured to receive measurements from said sensor;
- (f) a power storage device;
- (g) a thermoelectric generator connected to said power storage device; and
- (h) a wireless transmitter.

29. The apparatus set forth in claim 28, wherein said power storage device comprises a nickel-metal hydride battery.

30. The apparatus set forth in claim 28, wherein said source comprises an exhaust pipe and said thermoelectric generator comprises a thermoelectric sleeve configured to engage said exhaust pipe.

* * * * *